United States Patent
Roizen et al.

[19]

[11] Patent Number: 5,961,469
[45] Date of Patent: Oct. 5, 1999

[54] SPECTROPHOTOMETRIC ASSAY FOR CYANIDE

[76] Inventors: Michael F. Roizen, 5622 S. Woodlawn; Jon Moss, 5827 S. Blackstone, both of Chicago, Ill. 60637

[21] Appl. No.: 08/749,032

[22] Filed: Nov. 14, 1996

Related U.S. Application Data

[60] Provisional application No. 60/007,397, Nov. 21, 1995.

[51] Int. Cl.[6] ..................................................... A61B 5/00
[52] U.S. Cl. .......................... 600/531; 436/66; 422/44; 356/39; 600/322; 600/532
[58] Field of Search ................ 436/66; 422/44, 422/39; 356/40, 41; 600/322, 323, 326, 328, 336, 329, 531, 532; 604/4–6

[56] References Cited

U.S. PATENT DOCUMENTS

| | | | |
|---|---|---|---|
| 4,083,367 | 4/1978 | Portner et al. | 600/538 |
| 4,706,676 | 11/1987 | Peck | 128/632 |
| 4,821,733 | 4/1989 | Peck | 128/636 |
| 4,853,338 | 8/1989 | Benezra et al. | 436/66 |
| 4,876,205 | 10/1989 | Green et al. | 436/66 |
| 4,880,749 | 11/1989 | Burdick et al. | 436/66 |
| 5,116,759 | 5/1992 | Klainer et al. | 436/68 |
| 5,468,640 | 11/1995 | Benezra et al. | 436/66 |
| 5,529,934 | 6/1996 | Chellanduri et al. | 436/69 |

OTHER PUBLICATIONS

Tung et al., "A New Rapid Assay To Measure Cyanide in Biological Fluids," Anesthesia, Sep., 1996, vol. B5, No. 3A, p. A233.

*Primary Examiner*—Robert L. Nasser
*Attorney, Agent, or Firm*—Roberts & Brownell, LLC

[57] ABSTRACT

A method of detecting and quantifying cyanide concentration in a patient, by monitoring photometric changes resulting from the transformation of methemoglobin to cyanomethemoglobin. The present invention provides for a means of cyanide poisoning assessment in patients using the affinity of methemoglobin for cyanide to assess the photometric changes resulting from methemoglobin converting to cyanomethemoglobin, as an indicator of cyanide concentration in a patient. Appropriate corrective action can then be promptly taken.

31 Claims, 6 Drawing Sheets

SPECTROPHOTOMETRIC ASSAY FOR CYANIDE

RELATED APPLICATION DATA

The present disclosure is a non-provisional application related to the provisional U.S. patent application entitled "Spectrophotometric Assay for Cyanide", Ser. No. 60/007,397, filed Nov. 21, 1995.

FIELD OF THE INVENTION

This invention relates generally to a method for rapidly assessing the cyanide concentration in a patient, allowing for the timely administration of an appropriate treatment. More specifically, this invention relates to a means of measuring cyanide in either blood, cutaneously transpired gas or exhaled gas.

BACKGROUND OF THE INVENTION

Clinical diagnosis of cyanide poisoning is complicated by the lack of an easy, convenient assay for cyanide concentration in a patient. Therapy may be delayed with an unconfirmed diagnosis because the conventional antidote to cyanide poisoning exposes patients to substantial risks. Where the patient is not suffering from cyanide poisoning, administration of the antidote may cause patient death. However, delay in treatment may also result in patient death. The present invention is related to a means of diagnosing cyanide poisoning.

Molecules of oxygen enter the body through the respiratory organs and are transported to cells by the blood (oxyhemoglobin). The oxygen is used by cell organelles in the process of releasing energy from glucose molecules with the energy made available being used for a variety of cell activities. A continuing supply of oxygen is necessary for cell survival, and ultimately for the survival of an organism. Cyanide binds to the intracellular proteins (cytochromes) responsible for cellular respiration. Inhibition of cellular respiration by cyanide causes cell death by depriving cells of the ability to use oxygen.

Hemoglobin has a complex molecular structure that consists of two portions, heme and globin. The heme portion contains four atoms of iron, each of which can combine loosely with an oxygen molecule, forming oxyhemoglobin. The amount of oxygen that combines is determined by the concentration of oxygen. Because the chemical bonds that form between oxygen and hemoglobin are relatively unstable, oxygen is released from the hemoglobin molecule as the concentration of oxygen decreases. The oxygen can then diffuse from the blood into nearby cells. This necessary oxygen supply can be compromised by the presence of the $CN^-$ ion.

Oral ingestion of cyanogenic plants such as Cassava plants and apricot or peach seeds; cutaneous absorption; inhalation of smoke or industrial fumes and the breakdown of sodium nitroprusside can all introduce the $CN^-$ ion into the blood stream. Methemoglobin is a naturally occurring breakdown product of hemoglobin, which usually occurs in low concentrations in normal blood. While methemoglobin does not normally function to carry oxygen, it has increased affinity for $CN^-$ (the cyanide ion), and thus can scavenge $CN^-$ preferentially over normal hemoglobin.

Several methods of treating cyanide poisoning are known to those skilled in the art. One such method converts endogenous hemoglobin to methemoglobin with sodium nitrite. The methemoglobin removes cyanide ions from the various tissues and couples with them to become cyanomethemoglobin, a compound having relatively low toxicity. The bound CN is then excreted in the urine or retained until natural elimination can catabolize it. Sodium nitrite is, however, associated with hypotension which can be severe in hypovolemic patients. Additionally, the methemoglobinemia produced by sodium nitrite can also significantly decrease oxygen delivery and worsen tissue hypoxia in patients already compromised by coexisting carbon monoxide poisoning.

A second method of CN detoxification enhances the natural elimination pathway. The natural elimination pathway reacts CN with disulfide bonds to form thiocyanate endogenously, which can then be excreted in the urine. The enzymes responsible for this reaction have not been completely described, however, a primary one is rhodanese located mainly in the liver. During natural elimination, the disulfide bonds come from the body's sulfur-sulfane pool and include thiosulfate. To assist natural elimination a compound such as sodium thiosulfate or methylene blue (tetramethylthionine chloride) is administered, and aids in the conversion of cyanide to thiocyanate. Administration of exogenous thiosulfate is believed safe and effective. However, given alone, this type of compound acts too slowly for acute, critically ill patients.

The standard cyanide antidotal therapy in the United States (Taylor Pharmaceuticals, San Clemente, Calif.) is designed for pure cyanide poisoning and employs both thiosulfate and nitrites to induce methemoglobin formation from endogenous hemoglobin, thereby decreasing oxygen carrying capacity in the blood. This therapy includes administration of amyl nitrite, sodium nitrite and sodium thiosulfate. Amyl nitrate is applied by opening an ampule and holding it in front of the patients mouth for approximately 15 seconds. After a 15 second rest, the ampule is again placed in front of the patients mouth. This cycle is repeated until sodium nitrite can be administered. 300 mg of sodium nitrite is administered intravenously (10 milliliters in three percent solution) at a rate of 2.5 to 5 ml/min. The recommended dose of sodium nitrite for children is 6 to 8 ml/square meter (approximately 0.2 ml/kg of body weight) but is not to exceed 10 ml. Sodium thiosulfate is then injected. The dosage for adults is 12.5 grams of sodium thiosulfate (50 milliliters of 25 percent solution). The dosage for children is 7 g/square meter of body surface area, but dosage should not exceed 12.5 grams. Where the poison is taken by mouth, gastric lavage is performed, either concurrently with the above listed treatments by a third person or after administration of the above listed treatments.

Prior to implementation of treatment, particularly when the treatment itself is of high risk, a diagnosis of the condition must be determined. While the physiological effects of cyanide poisoning are well known, the clinical diagnosis is often complicated by nonspecific symptoms and the lack of an easy, convenient assay for cyanide concentration in the blood. Given the risks associated with known treatments for cyanide poisoning, there exists a need for a noninvasive means of treating this condition that is of lower risk to the patient. Methods known in the art for determining cyanide levels in blood generally involve acidification of the sample and trapping the resultant HCN gas into an alkali solution. The trap solution is then quantified through a means such as chemical color change, potentiometry, chromatography or polarography. None of the existing procedures for the quantitation of cyanide levels in serum are rapid or available enough to alter therapeutic decisions, most require special expertise or equipment. In many hospitals, a cyanide assay can take hours to days or may not be available at all. In the absence of a laboratory test for cyanide, the diagnosis of acute toxicity is usually made from patient history and physical examination, which may be nonspecific Cyanide poisoning can be rapidly fatal. Patients with severe poisoning may only survive a brief time. Thus, for effective treatment, antidote administration should occur as quickly as possible. However, in light of the substantial risks associated with known treatments for cyanide poisoning, therapy may be delayed because of diagnosis uncertainty. There thus exists a need for an accurate and rapid means of confirming cyanide poisoning.

SUMMARY OF THE INVENTION

It is therefore an object of the present invention to provide a rapid means for confirming cyanide poisoning that is accurate and precise throughout the clinically relevant range of cyanide concentrations.

It is a further object of the present invention to provide an accurate and rapid means for confirming cyanide poisoning that requires only readily available hospital equipment.

It is a further object of the present invention to provide a noninvasive means of confirming cyanide poisoning.

It is a further object of the present invention to provide a test for cyanide poisoning that is not compromised by the presence of thiosulfate.

It is a further object of the present invention to provide a noninvasive means of treating cyanide poisoning.

These and other objects of the present invention will become obvious to those skilled in the art upon review of the following disclosure.

A method of detecting cyanide in blood in accordance with the present invention includes acidifying a blood sample, trapping any resulting hydrogen cyanide gas, buffering the solution, adding methemoglobin and monitoring any photometric changes. In alternative embodiments cyanide is detected in exhaled gas and/or cutaneously transpired gas. In another alternative embodiment the level of cyanide present in blood, exhaled gas and/or cutaneously transpired gas is quantified. A method of treating cyanide poisoning in accordance with the present invention includes applying a methemoglobin solution to portions of the patient's skin.

DETAILED DESCRIPTION

Figure 1:
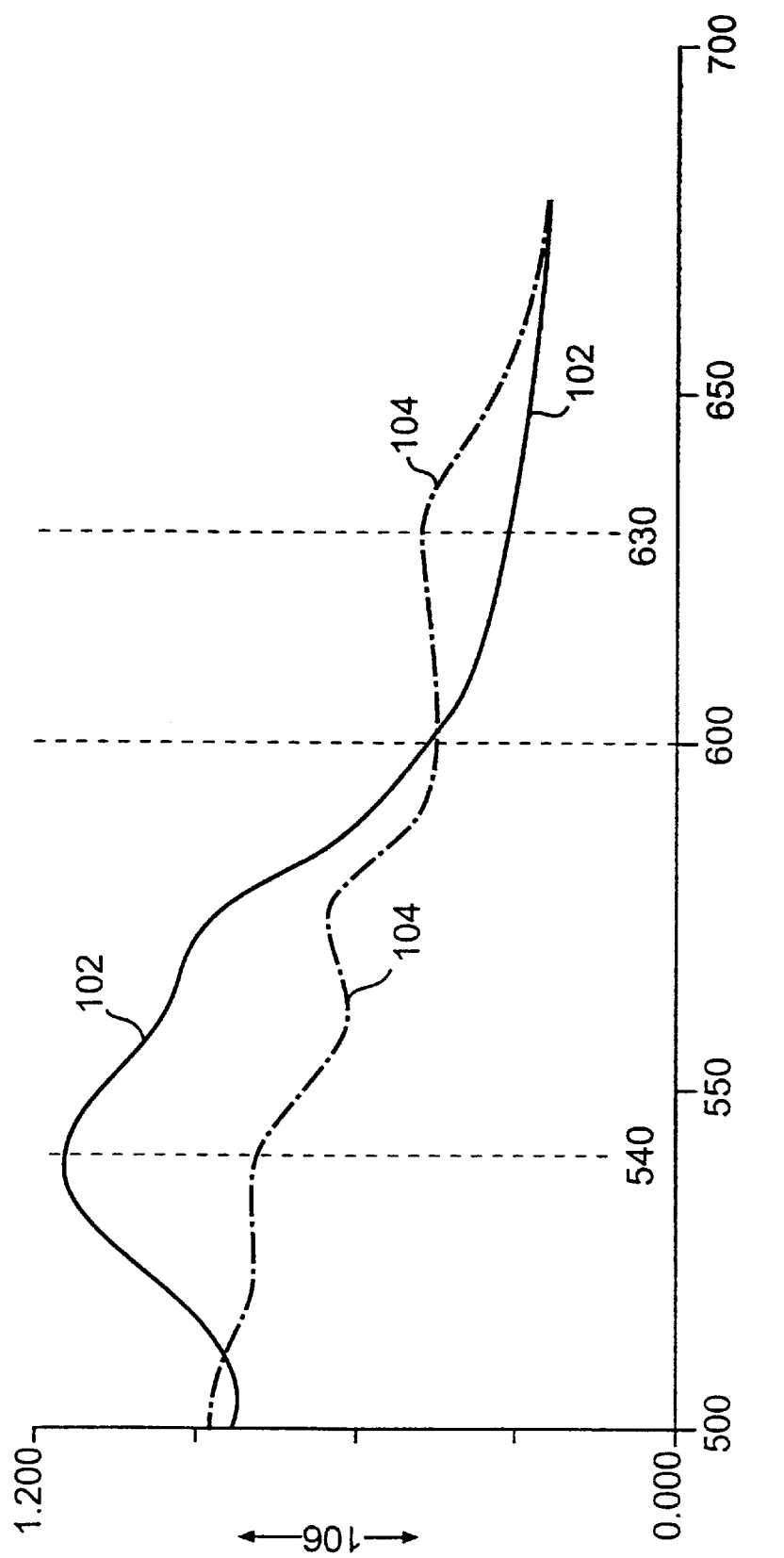
FIG. 1 depicts the absorbance spectrum for cyanomethemoglobin and methemoglobin.
Figure 2:
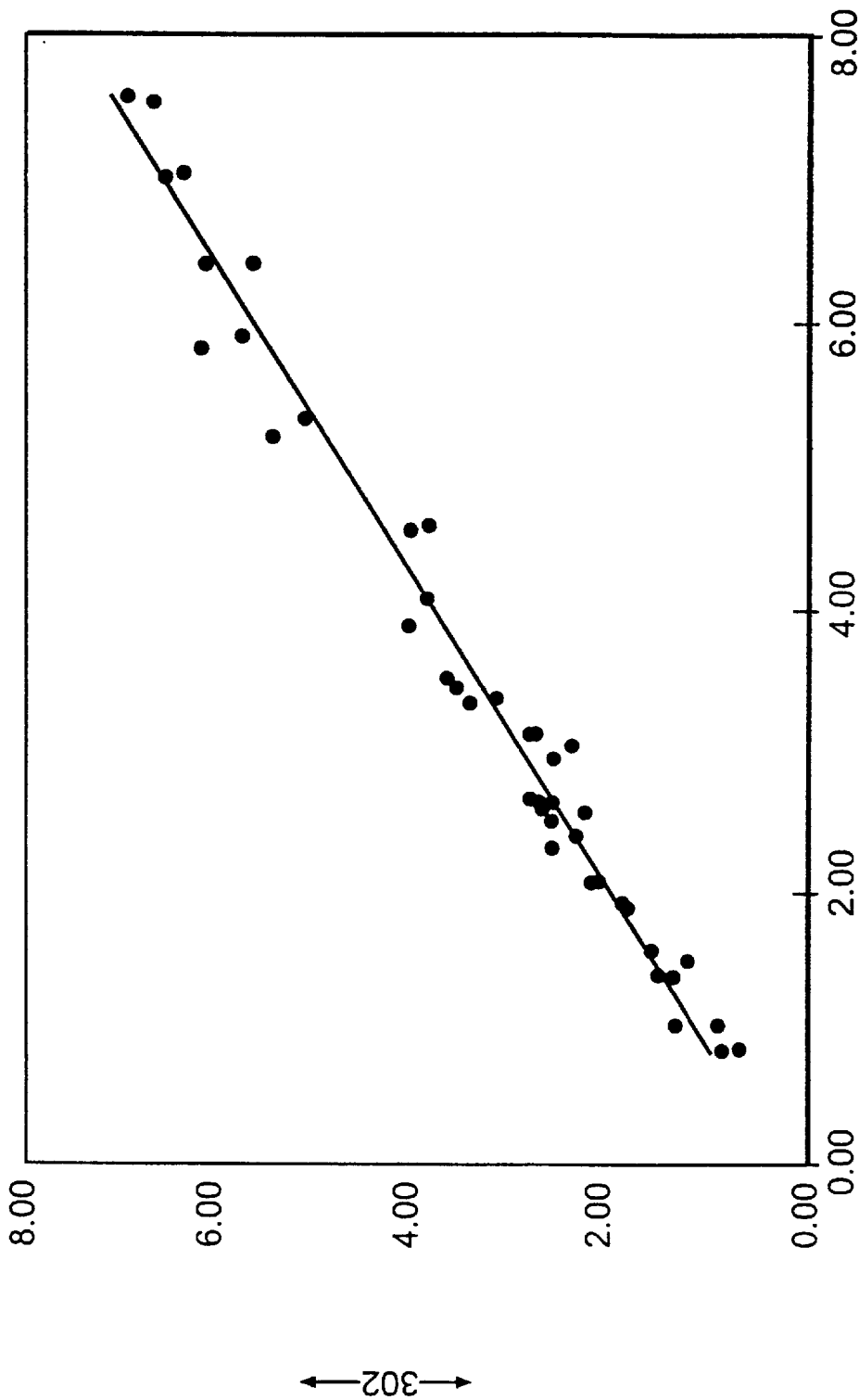
FIG. 2 compares results of cyanide solutions in 0.1 N sodium hydroxide obtained through methemoglobin assay with those obtained through polarography.

The present invention makes use of the affinity of cyanide for the methemoglobin molecule and the differing absorption characteristics of cyanomethemoglobin and methemoglobin, as a means of detecting and quantitating cyanide. FIG. 1 depicts the absorbance spectrum for cyanomethemoglobin 102 and methemoglobin 104 in a one centimeter light path, with absorbance (A) 106 plotted on the vertical axis and wavelength (nm) 108 plotted on the horizontal axis. Formation of cyanomethemoglobin results in a decrease in absorbance 106 at 630 nm, and an increase in absorbance 106 at 540 nm. No change in absorbance 106 is noted at 600 nm.

In practice, cyanide is extracted from blood samples by acidifying the blood and solubilizing the cell membranes. The resulting HCN gas is swept into a trap solution. The solution is buffered and then brought to a pH of approximately 6.5–8.0 through the addition of an acid. Methemoglobin solution is then added. Solution absorbance is read at 630, 600 and 540 nm. Samples of external standards are assayed with each group of blood sample measurements. Internal standards are added to each blood sample.

The preferred embodiment of the present invention is described as follows:

External Standard

The external standard solutions range from 4.6 nmol/cc to 115.5 nmol/cc. These are made by dissolving potassium cyanide in an alkali solution. In alternative embodiments, the alkali solution contains an alkali such as sodium hydroxide, potassium hydroxide or calcium hydroxide. The resulting solution is then stored. In an alternative embodiment, the resulting solution is stored in polyethylene screw-capped tubes.

Internal Standard 50 to 100 µl aliquots of internal standard are added to each blood sample. In an alternative embodiment, the internal standard comprises a one millimolar solution of potassium cyanide (Aldrich Chemical Co., Milwaukee, Wis.) in distilled water. In additional alternative embodiments the internal standard comprises about 25–100 mg per cc without any difference in the efficacy of the assay.

Methemoglobin Solution

Methemoglobin is dissolved in a buffer such as sodium phosphate or potassium phosphate, to a desired concentration. In an alternative embodiment, lyophilized methemoglobin crystals (ICN Biochemicals, Aurora, Ohio) are dissolved in 50 mM sodium phosphate at pH 7.0 to a final concentration of 50 mg/cc. 50 mg/cc of methemoglobin is ideal for the range of human toxicity in blood, tissue or gas, however, more or less may be required, and the sensitivity is dependent upon the cyanide concentration. Levels lower than about 10 mg/cc are not effective.

The degree of color change resulting from cyanomethemoglobin formation represents the fraction of methemoglobin bound to cyanide. Lower concentrations of methemoglobin will therefore manifest a greater color change for a given amount of cyanide than higher methemoglobin concentrations because a higher percentage of methemoglobin will be bound to cyanide. If an insufficient amount of methemoglobin is used, an excess of unbound cyanide may remain and will not be measured. In a preferred embodiment, a methemoglobin concentration of 2 mg/cc of alkali trap solution has a sensitivity of 300 ng/cc and is linear up to 7 mg/cc cyanide.

In additional alternative embodiments the pH may be from about 6.5 to about 8 without any change in the efficacy of the assay.

Acidification

An equal amount of distilled water is added to each sample to facilitate disruption of red blood cells. A dispersive agent is added. In an alternative embodiment, the dispersive agent is a nonionic surfactant. In another alternative embodiment, the dispersive agent is one hundred microliters of a 1:10 solution of Triton X100 (JT Baker Chemical Co., Philipsburg, N.J.)((CH3)3CCH2C (CH3)2⊙O[CH2CH2O]$^N$H) in distilled water. The samples are vortexed to disrupt red blood cell membranes. In an alternative embodiment, the samples are vortexed for about 15 seconds. Following vortexing, the mixture is placed in a flask such as a 50 cc Erlenmeyer flask. An acidic solution such as hydrogen chloride, sulfuric acid or nitric acid is added. In an alternative embodiment one cc of a 1.0 N acidic solution such as hydrogen chloride is added.

Trapping Of Hydrogen Cyanide

The acidified mixture is stirred and air is passed over it to sweep the evolved hydrogen cyanide gas from the sample into a trap containing an alkali solution. In alternative embodiments, the alkali solution contains an alkali such as sodium hydroxide, potassium hydroxide or calcium hydroxide. In another alternative embodiment, one cc of 0.1 N sodium hydroxide is used. A gas flow of about 2 cc/sec is maintained for approximately thirty minutes. Tubing is used for gas transport between sample and trap, and the gassing train is periodically checked for airtightness. In an alternative embodiment, Teflon tubing (LKB-Produkter, Bromma, Sweden), 1.2 mm in diameter is used.

Assaying For Cyanide

The solution containing trapped cyanide is buffered. In alternative embodiments, a buffer such as sodium phosphate or potassium phosphate is added. In another alternative embodiment, 250 µl of 500 mM sodium phosphate (Fisher Scientific, Pittsburgh, Pa.) at pH 7.4 is added to buffer the solution. An acid such as hydrogen chloride is added to titrate the solution to pH 6.5–8.0. Approximately 40 µl of the methemoglobin solution, prepared under the conditions described above, is added to the buffered trap solution. The mixture is incubated at room temperature. In an alternative embodiment, approximately 10 minutes is required for complete binding at room temperature.. In another alternative embodiment, the mixture is incubated at 37° C. In this embodiment, binding is complete in approximately four to five minutes. However, it is technically more cumbersome to incubate at this higher temperature. In additional alternative embodiments, data is valid from approximately 20° C. to 37° C. with decreased incubation time required at the higher temperatures. Above 40° C. denaturation of protein can occur. There is no difference in the extent of color change as an effect of temperature.

In additional alternative embodiments, varying the final concentration of buffer in the sample from about 25 mM to about 100 mM did not affect the speed or the extent of the cyanide binding reaction. Samples of the external standards are assayed with each group of sample measurements.

Measuring Absorbance

Photometric changes of the blood sample may be measured visually or with the aid of a laboratory instrument such as a spectrophotometer.

The absorbance of the solution is read at 630, 600 and 540 nm using a spectrophotometer such as Perkin-Elmer Lambda 4B spectrophotometer (Norwalk, Conn.). The ratios of A630/A600 and A540/A600 are determined, with A630 being equal to the absorbance at 630 nm, A600 being equal to the absorbance at 600 nm and A540 being equal to the absorbance at 540 nm. The sum of the absorbance ratios (A630/A600+A540/A600) is plotted against cyanide concentration using known standards. The cyanide concentration in the sample is calculated by interpolation using linear regression.

In an alternative embodiment, a relationship which predicts the percent of cyanomethemoglobin in the methemoglobin solution is determined by solving the following simultaneous equations, where M equals methemoglobin and C equals cyanomethemoglobin:

Equation No. 1:

$$A600 = 3000(M + C);\ M + \frac{A600}{3000} - C$$

$$A630 = 4200M + 800C$$

$$C = \frac{1.4A600 - A630}{3400}$$

Equation No. 2:

$$A630 = 4200M + 800C$$

therefore, $$M = \frac{(A630 - 0.267A600)}{3400}$$

$$\text{Solving } \frac{C}{C+M} = \frac{1.4A600 - A630}{1.4A600 - A630 + A630 - 0.267A600}$$

Incorporating slope and intercept data, $$\text{percent } C = 124 - 90(A630/A600)\ [\text{between extremes 0-1}].$$

Figure 3:
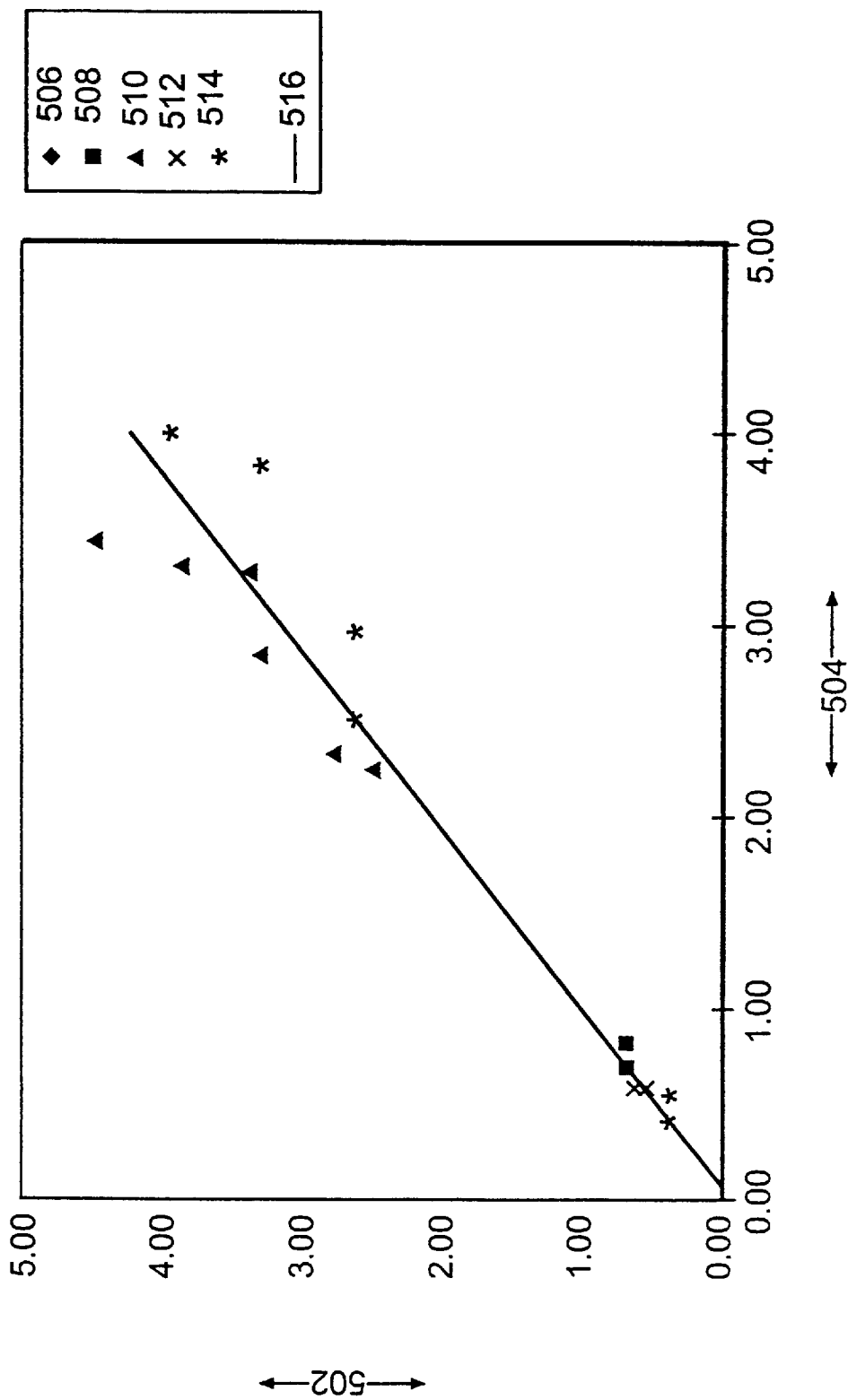
FIG. 3 compares results of cyanide in whole blood obtained through methemoglobin assay with those obtained through polarography.
Figure 4:
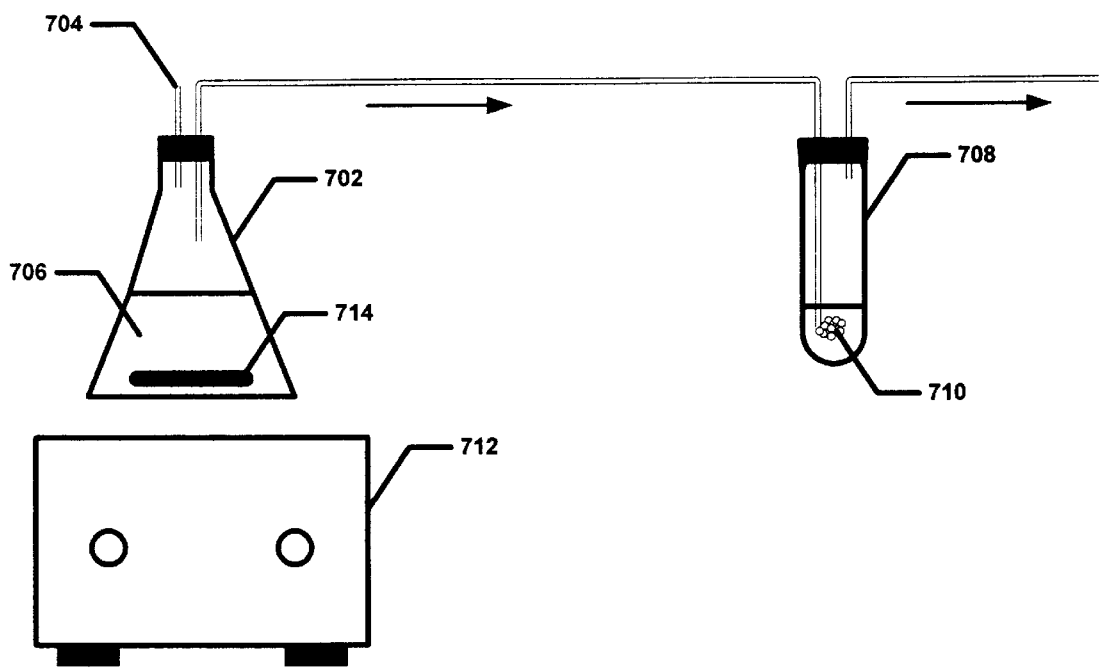
FIG. 4 depicts an apparatus for extraction of cyanide.

FIG. 3 compares spectrophotometric results of cyanide solutions in 0.1 N Sodium hydroxide acquired through methemoglobin assay with results acquired through polarography. Polarographic method results (µg/cc) 302 are plotted on the vertical axis and methemoglobin method results (µg/cc) 304 are plotted on the horizontal axis. The correlation coefficient (r) between methemoglobin method results (µg/cc) 304 and polarographic method results (µg/cc) 302 is 0.983 over a range from 1.49 µg/cc to 7.5 µµg/cc.

Figure 5:
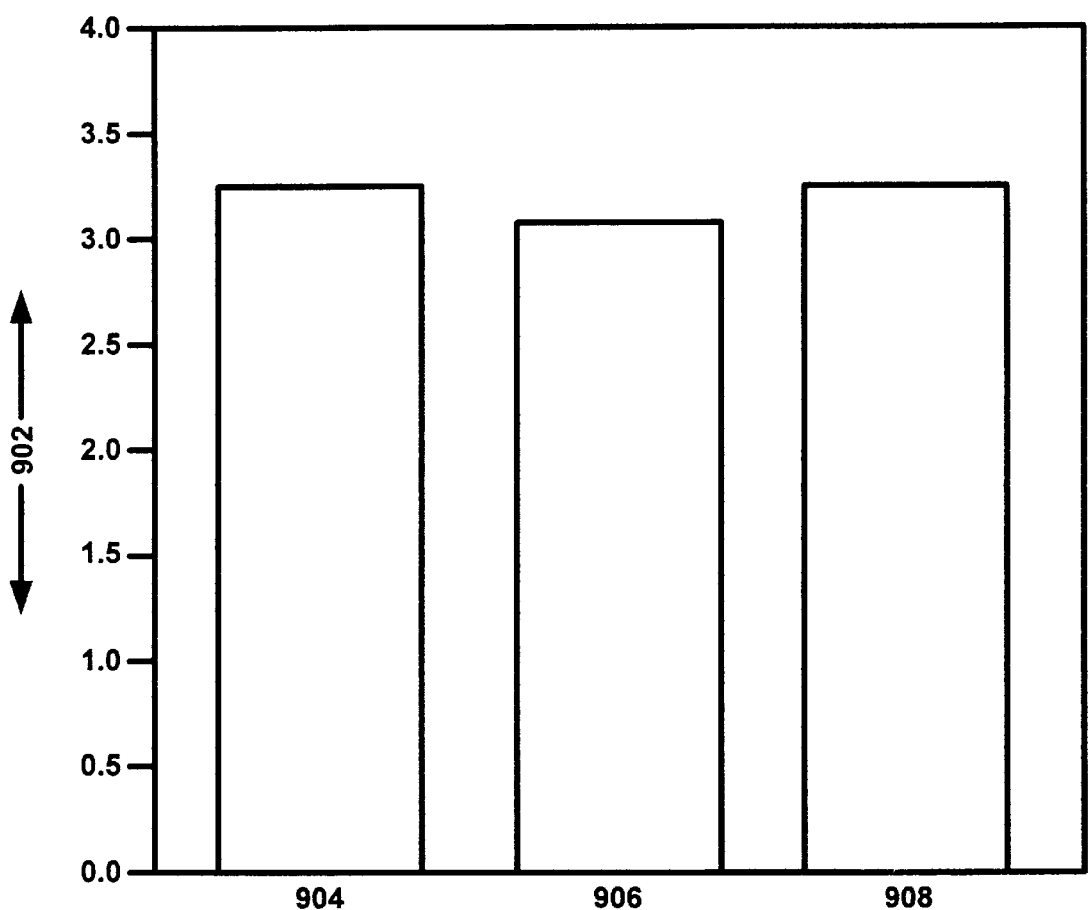
FIG. 5 compares cyanide measured in whole blood with cyanide measured in whole blood contaminated with thiosulfate.
Figure 6:
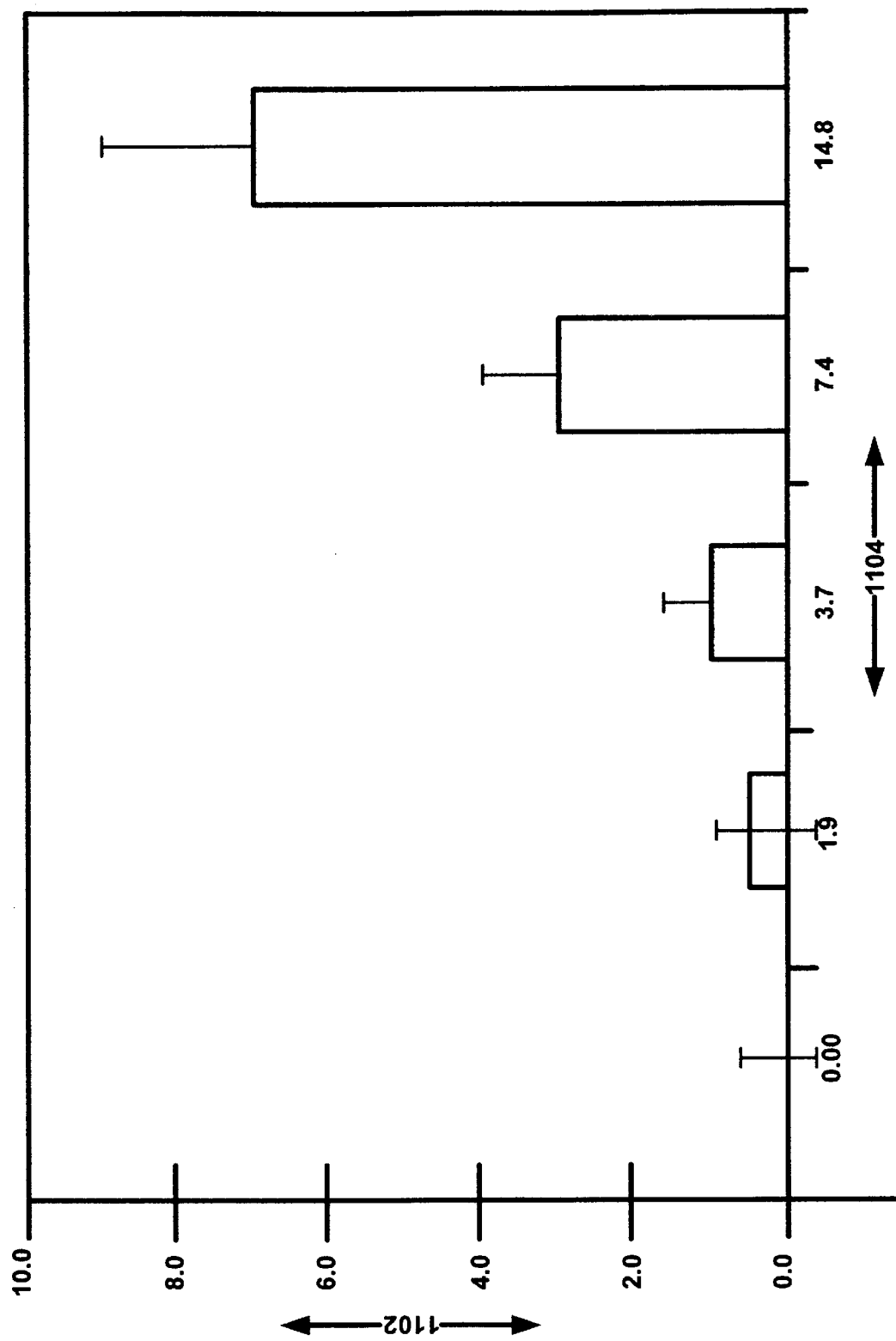
FIG. 6 depicts the spectral shift occurring with assay of cyanide by methemoglobin in circuit with expired gas.

FIG. 5 compares spectrophotometric results acquired through methemoglobin assay, from five patients receiving sodium nitroprusside (an antihypertensive which liberates cyanide) with results acquired through polarography. Polarographic method results 502 are plotted on the vertical axis and methemoglobin method results 504 are plotted on the horizontal axis. Comparison of results obtained by the methemoglobin method in each example to those obtained through polarography yielded correlation coefficient (r) 516 of 0.978.

EXAMPLE ONE

First patient 506 was a 40 year old female with chronic renal failure receiving sodium nitroprusside at doses between 1 and 2.6 µg/kg/min for control of malignant hypertension. Samples were drawn after 12 hours of nitroprusside therapy.

EXAMPLE TWO

Second patient 508 was a 60 year old male with hypertension and congestive heart failure receiving sodium nitroprusside in a dosage range from 0.6–1.2 µg/kg/min for afterload reduction. Samples were drawn after 8 hours of nitroprusside therapy.

EXAMPLE THREE

Third patient 510 was a 69 year old male with mitral regurgitation and hypertension receiving sodium nitroprusside for afterload reduction at doses between 1 and 2.5 μg/kg/min. Samples were drawn after 18 hours of therapy.

EXAMPLE FOUR

Fourth patient 512 was a 71 year old female with hypertension admitted for evaluation of an aortic dissection. Nitroprusside was administered in a dosage range from 0.7 to 3.0 μg/kg/min for control of blood pressure. Samples were drawn after 20 hours of therapy.

EXAMPLE FIVE

Fifth patient 514 was a 63 year old female with hypertension also admitted for dissecting aortic aneurysm. Nitroprusside was administered at doses between 1.0 and 5.0 μg/kg/min for blood pressure control. Samples were drawn after 30 hours of therapy.

Normal plasma cyanide levels in non-smokers has been reported between 4–20 ng/cc. Toxic levels are commonly reported between 1–7 μg/cc depending upon the clinical situation. In practicing the present invention, the lower limit of detection is about 150 ng/cc and incremental increases of about 50 ng/cc can be detected.

FIG. 7 depicts an apparatus for extraction of cyanide into an alkali solution. Air is drawn into Erlenmeyer flask 702 through port 704 and passed over sample 706 sweeping the evolved hydrogen cyanide gas from sample 706 into trap 708 containing alkali solution 710. Stir plate 712 causes stir bar 714 to stir sample 706.

A potential problem with the measurement of cyanide in whole blood is contamination with the less toxic thiocyanate metabolite. In normal human metabolism, cyanide is converted to thiocyanate in the liver and excreted by the kidney. As the usual molar ratio of thiocyanate to cyanide in blood plasma is approximately 50:1, cross reactivity can cause an assay to seriously overestimate cyanide levels. However, the addition of thiocyanate to blood containing cyanide does not change the specificity of the assay of the present invention for cyanide. FIG. 9 depicts cyanide measured (μg/cc) 902 in whole blood. First example 904 depicts cyanide measured 902 from a sample containing 3.25 μg/cc cyanide. Second example 906 depicts cyanide measured 902 from a sample containing 3.25 μg/cc cyanide with 50 nM/cc thiosulfate. Third example 908 depicts cyanide measure 902 from a sample containing 3.25 μg/cc cyanide with 75 nM/cc thiosulfate. There is no difference in the measured level of cyanide when either 50 nmol/cc or 75 nmol/cc thiocyanate is added to blood containing cyanide.

In an alternative embodiment, cyanide is detected and quantified from exhaled gas. To monitor exhaled gas, the patient first blows into the mouthpiece of a hollow chamber. Within the chamber is a matrix that contains methemoglobin. In alternative embodiments, the matrix is either a solid, such as filter paper, impregnated with methemoglobin or a solution containing methemoglobin. As the methemoglobin reacts with cyanide, cyanomethemoglobin is formed. As mentioned, cyanomethemoglobin has differing spectrophotometric characteristics than does methemoglobin. These differing characteristics cause a change to the matrix that can be monitored either visually or spectrophotometrically. In an alternative embodiment, due to this photometric change the matrix changes color from a red to a ruddy brown. In another alternative embodiment, due to this photometric change the matrix changes color from bright red to dark red.

FIG. 11 depicts the spectral shifts occurring with assay of cyanide by methemoglobin in circuit with expired gas. Spectral shift 1102 is plotted on the vertical axis. Dose (μmol/min) 1104 is plotted on the horizontal axis.

In an alternative embodiment, cyanide is detected and/or quantified from cutaneously transpired gas. To monitor cutaneously transpired gas, a transdermal detection system such as that disclosed in U.S. Pat. Nos. 4,821,733 and 4,706,676 to Peck which is herein incorporated by reference, is applied to the skin. In this embodiment the porous carrier of the transdermal detection system is impregnated with methemoglobin. Where cyanide is present in the cutaneously transpired gas, the methemoglobin reacts with the cyanide forming cyanomethemoglobin. The corresponding photometric change may be monitored either visually or spectrophotometrically.

METHOD OF TREATMENT

Following assessment of the patient's cyanide concentration, therapy is initiated to inactivate or detoxify the cyanide or to limit exposure. This therapy can include administering the Cyanide Antidote Kit (Taylor Pharmaceuticals, San Clemente, Calif.) as discussed in the background of this application.

In the present invention, therapy comprises administering stroma-free methemoglobin to the skin of patients. In alternative embodiments, a solution containing stroma-free methemoglobin is either painted on the patient's skin with a brush or administered through an aerosol. Due to the affinity of methemoglobin for cyanide, administration of stroma free methemoglobin to the patient's skin effectively draws the cyanide from the patient.

Although the methods of the present invention have been described in detail for purpose of illustration, it is understood that such detail is solely for that purpose, and variations can be made therein by those skilled in the art without departing from the spirit and scope of the invention.

What is claimed is:

1. A method of detecting cyanide in blood comprising:
   (a) acidifying a blood sample, wherein the blood sample comprises red blood cells and red blood cell membranes, to form an acidified sample;
   (b) trapping any hydrogen cyanide gas that forms in the acidified sample to form a trapped solution;
   (c) buffering the trapped solution to form a buffered trapped solution;
   (d) adding methemoglobin to the buffered trapped solution;
   (e) measuring any photometric change of the blood sample; and
   (f) taking corrective action to counter toxic levels of cyanide present.

2. A method of detecting cyanide in blood as claimed in claim 1 wherein the measuring any photometric change comprises:
   visually identifying any color change of the blood sample.

3. A method of detecting cyanide in blood as claimed in claim 1, wherein the monitoring any photometric change comprises:
   measuring absorbance with a spectrophotometer.

4. A method of detecting cyanide in blood as claimed in claim 3, wherein measuring of absorbance occurs at 630 nm, 600 nm and 540 nm.

5. A method of detecting cyanide in blood as claimed in claim 4, further comprising:

quantifying cyanide concentration in the blood sample.

6. A method of detecting cyanide in blood as claimed in claim 5, wherein cyanide quantifying comprises:

(a) determining a first ratio of the absorbance at 630 nm to the absorbance at 600 nm;

(b) determining a second ratio of the absorbance at 540 nm to the absorbance at 600 nm;

(c) adding the first ratio to the second ratio to derive a sum of absorbance ratios;

(d) plotting the sum of absorbance ratios against cyanide concentration using known standards; and (e) calculating cyanide concentration by interpolation using linear regression.

7. A method of detecting cyanide in blood as claimed in claim 5, wherein cyanide quantifying comprises:

solving the equation 124−90(A630/A600), wherein A630 is the absorbance at 630 nanometers and A600 is the absorbance at 600 nanometers.

8. A method of detecting cyanide in blood as claimed in claim 1, wherein acidifying a blood sample further comprises:

adding an acid selected from the group consisting of hydrogen chloride, sulfuric acid and nitric acid.

9. A method of detecting cyanide in blood as claimed in claim 1, wherein trapping any resulting cyanide further comprises:

(a) placing the acidified sample into a flask;

(b) drawing air into the flask through a port; and (c) passing the air over the acidified sample, wherein the air passage sweeps evolved hydrogen cyanide gas from the acidified sample to a trap.

10. A method of detecting cyanide in blood as claimed in claim 8, wherein the trap contains an alkali solution, the alkali selected from the group consisting of sodium hydroxide, potassium hydroxide, and calcium hydroxide.

11. A method of detecting cyanide in blood as claimed in claim 1, wherein buffering the trapped solution further comprises:

adding a buffer selected from the group consisting of sodium phosphate and potassium phosphate.

12. A method of detecting cyanide in blood as claimed in claim 1, further comprising:

disrupting the red blood cells.

13. A method of detecting cyanide in blood as claimed in claim 12, wherein disrupting the red blood cells further comprises:

adding distilled water to the blood sample.

14. A method of detecting cyanide in blood as claimed in claim 13, further comprising: adding a dispersive agent.

15. A method of detecting cyanide in blood as claimed in claim 14, wherein the dispersive agent is a nonionic surfactant.

16. A method of detecting cyanide in blood as claimed in claim 14, wherein the dispersive agent is a 1:10 solution of Triton X100 in distilled water.

17. A method of detecting cyanide in blood as claimed in claim 1, further comprising:

adding an internal standard to each blood sample.

18. A method of detecting cyanide in blood as claimed in claim 17, wherein the internal standard comprises potassium cyanide in distilled water.

19. A method of detecting cyanide in blood as claimed in claim 1, wherein the corrective action comprises:

applying methemoglobin solution to portions of the patients skin.

20. A method of detecting cyanide in exhaled gas comprising:

(a) blowing into a breath analyzer, wherein the breath analyzer comprises:

a mouthpiece;

a hollow chamber connected to the mouthpiece; and a matrix containing methemoglobin within the hollow chamber; and (b) measuring the matrix for photometric change indicative of the presence of cyanomethemoglobin.

21. A method of detecting cyanide in exhaled gas as claimed in claim 20 wherein the matrix is a solid.

22. A method of detecting cyanide in exhaled gas as claimed in claim 21 wherein the solid is filter paper.

23. A method of detecting cyanide in exhaled gas as claimed in claim 20, wherein the matrix is a liquid.

24. A method of detecting cyanide in exhaled gas as claimed in claim 20, wherein measuring the matrix for photometric change comprises:

visually identifying any color change of the material impregnated with methemoglobin.

25. A method of detecting cyanide in exhaled gas as claimed in claim 20, wherein measuring the matrix for photometric change comprises:

measuring absorbance with a spectrophotometer.

26. A method of detecting cyanide in exhaled gas as claimed in claim 25, wherein the measuring of absorbance occurs at 630 nm, 600 nm and 540 nm.

27. A method of detecting cyanide in exhaled gas as claimed in claim 26, further comprising the step:

quantifying cyanide concentration in the blood sample.

28. A method of detecting cyanide in exhaled gas as claimed in claim 27, wherein quantifying cyanide further comprises:

(a) determining a first ratio of the absorbance at 630 nm to the absorbance at 600 nm;

(b) determining a second ratio of the absorbance at 540 nm to the absorbance at 600 nm;

(c) adding the first ratio to the second ration to derive a sum of absorbance ratios;

(d) plotting the sum of absorbance ratios against cyanide concentration using known standards; and (e) calculating cyanide concentration by interpolation using linear regression.

29. A method of detecting cyanide in exhaled gas as claimed in claim 27, wherein cyanide quantifying further comprises:

solving the equation 124−90(A630/A600), wherein A630 is the absorbance as 630 nanometers and A600 is the absorbance at 600 nanometers.

30. A method of detecting cyanide in exhaled gas as claimed in claim 20, further comprising:

taking corrective action to counter any cyanide present.

31. A method of detecting cyanide in exhaled gas as claimed in claim 30, wherein the corrective action comprises:

applying methemoglobin solution to portions of a patients skin.

* * * * *